United States Patent [19]

Sellstedt et al.

[11] 4,112,094
[45] Sep. 5, 1978

[54] N-(2-PYRAZINYL) 1H- (OR 2H) TETRAZOLE-5-CARBOXAMIDE DERIVATIVES FOR THE PREVENTION OF IMMEDIATE TYPE HYPERSENSITIVITY REACTIONS

[75] Inventors: John H. Sellstedt, Pottstown; Charles J. Guinosso, King of Prussia, both of Pa.; Albert J. Begany, Tuscon, Ariz.

[73] Assignee: American Home Products Corporation, New York, N.Y.

[21] Appl. No.: 815,972

[22] Filed: Jul. 15, 1977

Related U.S. Application Data

[63] Continuation-in-part of Ser. No. 669,562, Mar. 23, 1976, Pat. No. 4,044,144, which is a continuation-in-part of Ser. No. 542,465, Jan. 20, 1976, Pat. No. 3,966,965, which is a continuation-in-part of Ser. No. 344,466, Mar. 23, 1973, abandoned.

[51] Int. Cl.² .................. A61K 31/495; C07D 403/02
[52] U.S. Cl. ...................................... 424/250; 544/405
[58] Field of Search ................. 424/250; 260/250 BN

[56] References Cited

U.S. PATENT DOCUMENTS 4,041,032  8/1977  Murakami et al. ........... 260/250 BN

*Primary Examiner*—Leonard Schenkman
*Attorney, Agent, or Firm*—Richard K. Jackson

[57] ABSTRACT

Anti-allergic agents of N-(2-pyrazinyl) 1H- (or 2H) tetrazole-5-carboxamide derivation present the following formulae:

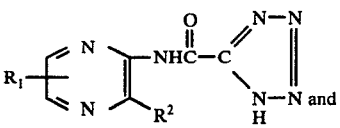

and

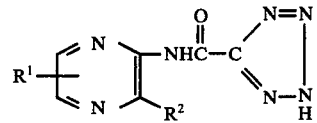

in which $R^1$ is hydrogen, lower alkylamino, di(lower)alkylamino, cyano, halo, lower alkyl or halo; and $R^2$ is hydrogen or cyano;

or a pharmaceutically acceptable salt thereof.

6 Claims, No Drawings

N-(2-PYRAZINYL) 1H- (OR 2H) TETRAZOLE-5-CARBOXAMIDE DERIVATIVES FOR THE PREVENTION OF IMMEDIATE TYPE HYPERSENSITIVITY REACTIONS

RELATED APPLICATIONS

This application is a continuation-in-part of Ser. No. 669,562, filed Mar. 23, 1976 now U.S. Pat. No. 4,044,144, which is a continuation-in-part of Ser. No. 542,465, filed Jan. 20, 1976, now U.S. Pat. No. 3,966,965, which in turn is a continuation-in-part of Ser. No. 344,466, filed Mar. 23, 1973, now abandoned.

BACKGROUND OF THE INVENTION

Atopic immediate sensitivity is the chief manifestation found in animals suffering from bronchial asthma, seasonal pollinosis (e.g. hay fever), allergic rhinitis, urticaria, allergic conjunctivitis, food allergies and anaphylactoid reactions. The substances most frequently responsible for clinically manifest sensitivities are plant pollen, animal feathers and danders, dust, milk and wheat, whether inhaled or ingested. Atopic hypersensitivity is found in man, dog and other animals. Its occurrence is exceptionally found in the lower animals.

The presence of antibodies associated with atopic hypersensitivity reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigenic factor and is usually labile at about 56° C. after 2 hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitive reactions. In the rat, the homocytotropic antibody is responsible for atopic immediate hypersensitive reactions.

In theory, reagin, influences the cell membrane of a mast cell by reacting with an antigen, to initiate the reaction(s) within the mast cell which ultimately releases a mediator such as Bradykinin, SRS-A (slow reacting substance-A), histamine and other unknown substances. The mediator effects a change in surrounding cell wal permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immunosuppressant, (3) block the action of the mediators on the cell under attack by administration of anti-histaminics, anti-5-hydroxy-tryptamines (5 HT) or anti-inflammatories, or (4) stimulate the cell under attack to negate the action of the mediator through the action of bronchodilators such as Isuprel ® or a Xanthine.

A compound typifying anti-allergic activity by blocking reaction(s) within the mast cells, thereby preventing the production and release of mediators, is disodium cromoglycate. (INTAL ®).

DESCRIPTION OF THE INVENTION

In accordance with this invention, there is provided a process for preventing the release of pharmacological mediators from an immediate hypersensitivity reaction between reaginic type antibodies and an antigen, thereby preventing the symptoms manifest in bronchial asthma, seasonal pollinosis, allergic rhinitis, urticaria, allergic conjunctivitis, food allergy and anaphylactoid reactions of a sensitized animal, which comprises prophylactically administering to said animal an effective amount of a compound of the formula:

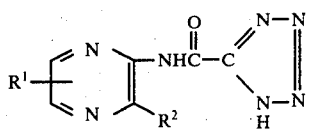

in which
$R^1$ is hydrogen, lower alkylamino, di(lower)alkylamino, cyano, halo, lower alkyl or halo; and
$R^2$ is hydrogen or cyano;
or a pharmaceutically acceptable salt thereof.

The novel N-(2-pyrazinyl)-1H-tetrazole-5-carboxamides form an additional aspect of this invention. They present the structural formula:

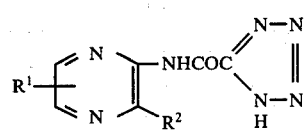

in which
$R^1$ is hydrogen, lower alkylamino, di(lower)alkylamino, cyano, halo, lower alkyl or halo; and
$R^2$ is hydrogen or cyano;
or a pharmaceutically acceptable salt thereof.

The term "lower" used throughout this application to modify alkyl, alkoxy, and the like, is intended to embrace univalent aliphatic hydrocarbon radicals containing from 1 to 6 carbon atoms. The term "halo" is used to embrace chlorine, bromine, iodine and fluorine. The expression "pharmaceutically acceptable salt" is intended to embrace acid addition salts, where applicable or 1H-tetrazole alkali metal or amine salts. Examples of acid addition salts include both organic and inorganic non-toxic salts formed with acids such as hydrochloric, hydrobromic, sulfuric, phosphoric, methane sulfonic, nitric, p-toluene sulfonic, acetic, citric, maleic, succinic acid and the like. The alkali metal or amine salts of the 1H-tetrazole include, sodium, potassium, lower alkylamine (e.g. methylamine, ethylamine, propylamine, etc.) di(lower)alkylamine (e.g. dimethylamine, diethylamine, dipropylamine, etc.), di(hydroxyethyl)amine, N,N¹-dibenzyl ethylene diamine, and the like.

The N-substituted tetrazole-5-carboxamide products of this invention may appear in either the 1H or 2H tautomeric forms. It is applicants' intention, throughout this specification and in the appended claims, to embrace the 2H tautomer as well as the 1H tautomer, both by the structural depiction of the 1H tautomer and by naming the 1H derivatives. The relationship between the tautomers is as follows:

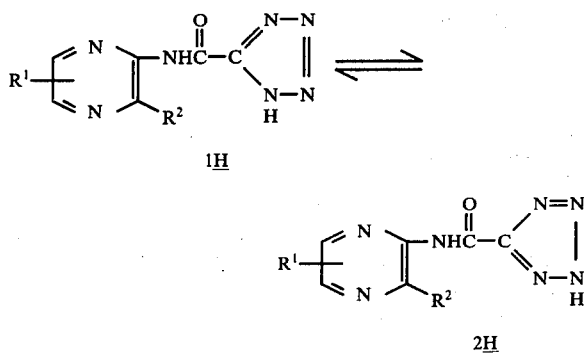

The compounds disclosed in this application relieve atopic allergic manifestations, when administered orally and parenterally to sensitized rats.

The technique employed to establish the anti-allergic activity of the 1H-tetrazole-5-carboxamide derivatives is reported in Immunology, vol. 16, pp 749–760 (1969) and involves four male Charles River rats (200–250 grams body weight) per group to provide a control, a host for administration of a standard anti-allergic compound (disodium cromoglycate) and animals for the test compound. The rats were injected intracutaneously on their shaved backs with sera from rats immunized with egg albumin and pertussis vaccine. Twenty-four hours after the initial injections, the test compound is administered intraperitoneally or orally at a dosage level of 200 milligrams per kilogram host body weight or less. Five minutes later one milliliter of a 0.5 percent solution of Evans blue dye and 8 milligrams of egg albumin is injected intravenously. After 40 minutes, the animal is sacrificed and the bleb size on its back is measured. The mean bleb size for the animals administered the test compound is calculated and the percent inhibition is determined by comparison with the control animal.

Although the mechanism by which the compounds of this invention function is not absolutely known, applicants believe that the compounds of this invention, in a manner similar to INTAL ®, block reaction(s) in the mast cell which lead to the production and release of mediators.

The compounds of this invention permit the occurrence of a non-productive antigen-antibody interaction. They effectively block the IgE type reaction and have little or no effect on the other immunoglobulins such as IgG, IgM, IgA and IgD.

In other words, the compounds of this invention block the release of mediators commonly resulting from the antigen-anti-body reaction as exemplified in a passive cutaneous anaphylaxis test (PCA) using rat homocytotropic antibody—a known correlate of human reaginic antibody.

By analogy to disodium cromoglycate and its activity correlation between standard test animals, domestic animals and man, the compounds of this invention have been established as anti-allergic agents suitable for the same uses at analogous doses and through the same route of administration as INTAL ®.

Thus, there is provided herewith a method for suppresing allergic manifestations of atopic immediate sensitivity in warm-blooded, human and non-human animals, the latter including domesticated animals such as the mouse, rat, hamster, gerbil, dog, cat, sheep, goat, horse, cow, and the like, by administering an effective amount of one or more of the compounds disclosed in this application by oral, topical, parenteral, rectal, vaginal or inhalation routes. The compounds of this invention may be administered in conjunction with known compounds effecting anti-histaminic, anti-hypertensive, analgesic, central nervous system depressant, immunosuppressive, anti-serotonin, anti-Bradykinin or endocrinological responses. In addition, those conventional adjuvants known to the art may be combined with the anti-allergics of this invention to provide compositions and solutions for administrative purposes, although it is considered desirable and feasible to employ the anti-allergics as neat or pure compounds without additives other than for purposes of providing suitable pharmaceutical solution or liquid or vapor suspensions, the latter for use as inhalants.

The oral dose range lies from below 0.1 milligram per kilogram to about 50 milligrams per kilogram host body weight. As an inhalant the dose is from that of INTAL ®, (about 20 milligrams) to 1/20th that quantity administered as needed prior to attack. Thus the dosage contemplated for human use based upon the potency of the compounds administered lies from about 5 milligrams to 1 gram, preferably 50 milligrams to about 750 milligrams in unit dosage form to be administered when necessary and to the degree of the desired response, in single or plural doses under the guidance of a physician.

An especially advantageous process for the production of the N-(2pyrazinyl)-1H- (or 2H) tetrazole-5-carboxamide derivatives of this invention, because of its broad applicability, involves reaction of the appropriately substituted 2-aminopyrazine reactant with 1-protected 1H-tetrazole-5-carbonyl chloride followed by deprotection (hydrogenolysis) and conversion to a pharmaceutically acceptable non-toxic salt as desired. The process is disclosed in U.S. Pat. No. 4,013,647, which disclosure is incorporated herein in its entirety.

The 2-aminopyrazine reactants employed in the preparation of the compounds of this invention are known or are readily prepared by methods known in the art. The N-(2-pyrazinyl)-1H-tetrazole-5-carboxamide derivatives of this invention have anti-allergic activity of the same potency order as the corresponding 2-pyridinyl-1H-tetrazole-5-carboxamide derivatives exemplified in Example 1.

EXAMPLE 1

N-(2-Pyridinyl)-1H-Tetrazole-5-Carboxamide, Sodium Salt 1-(4-Methoxybenzyl)-1H-tetrazole-5-carbonyl chloride (12.63 g., 0.05 mol) is dissolved in 310 ml. of methylene chloride and added to a 0°–5° solution of 4.71 g. (0.05 ml.) of 2-amino-pyridine and 4.18 ml. (0.052 ml.) of pyridine in 200 ml. of methylene chloride. The reaction solution is stirred 2 hr. at room temperature, washed twice with water, twice with brine, and dried with $CaCl_2$. Evaporation of the solvent and crystallization of the residue from acetonitrile gives 8.47 g. of 1-[(4-methoxyphenyl)methyl]-N-(2-pyridinyl)-1H-tetrazole-5-carboxamide, m.p. 111°–112°.

Analysis for: $C_{15}H_{14}N_6O_2$ — Calculated: C, 58.05; H, 4.35; N, 27.09. Found: C, 57.98; H, 4.40; N, 27.32.

The protected tetrazole (8.25 g., 0.0266 mol) and anisole 14.5 ml. (0.133 mol) are refluxed in 149 ml. of trifluoroacetic acid for ½ hr. under nitrogen, and the solution is then cooled in an ice bath. The solvent is removed on a rotary evaporator at 40°, and the residue is triturated with ether. The mixture is filtered and the filter cake is washed with ether giving a white solid, 5.40 g., m.p. 275° dec. The solid is stirred in water and acidified to pH$_2$ with 1NHCl, and the insoluble material is filtered, washed with water and dried at 60° over P$_2$O$_5$ in a vacuum. The white solid (3.06 g., 0.01609 mol) is then stirred in water and 16.1 ml. of 1.000N NaOH is added to give a solution which is filtered and freeze dried to give 3.27 g. of the title compound.

Analysis for: C$_7$H$_5$N$_6$NaO . H$_2$O — Calculated: C, 36.53; H, 3.07; N, 36.52. Found: C, 36.21; H, 3.18; N, 36.21.

The title compound exhibited the following dose-response relationship when administered to rats, intraperitoneally and orally, in the rat PCA test:

| dose mg/kg. i.p. | % inhibition |
|---|---|
| .01 | 24.8 |
| .1 | 41.9 |
| 1.0 | 82.6 |
| 10 | 99.0 |
| 100 | 72.5 |
| dose mg/kg. p.o. | % inhibition |
| .01 | 40.4 |
| .1 | 25.1 |
| 1.0 | 62.6 |
| 10 | 94.8 |
| 100 | 100.0 |

EXAMPLE 2

N-(2-Pyrazinyl)-1H-Tetrazole-5-Carboxamide, Sodium Salt 1-(4-Methoxybenzyl)-1H-tetrazole-5-carbonyl chloride is reacted in methylene chloride with 2-aminopyrazine to obtain N-(2-pyrazinyl)-1-(4-methoxybenzyl)-1H-tetrazole-5-carboxamide. The protected intermediate is deprotected and worked up by the techniques described in Example 1 to yield the title compound.

EXAMPLE 3

N-(5-Dimethylaminopyrazin-2-yl)-1H-Tetrazole-5-Carboxamide, Sodium Salt 1-(4-Methoxybenzyl)-1H-tetrazole-5-carbonyl chloride (0.05 mol) is reacted with 2-amino-5-(dimethylamino)pyrazine (0.05 ml.) in a manner similar to Example 1, and the intermediate protected tetrazole is deblocked to give the title compound.

EXAMPLE 4

N-(3-Cyanopyrazin-2-yl)-1H-Tetrazole-5-Carboxamide, Sodium Salt 1-(4-Methoxybenzyl)-1H-tetrazole-5-carbonyl chloride (0.05) is reacted with 2-amino-3-pyrazinonitrile (0.05 mol) in a manner similar to Example 1, and the intermediate protected tetrazole is deblocked to give the title compound.

What is claimed is:

1. A process for preventing the release of pharmacological mediators from an immediate hypersensitivity reaction between reaginic type antibodies and an antigen, thereby preventing the symptoms manifest in bronchial asthma, seasonal pollinosis, allergic rhinitis, urticaria, allergic conjunctivitis, food allergy and anaphylactoid reactions of a sensitized animal, which comprises prophylactically administering to said animal an effective amount of a compound of the formula:

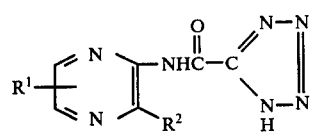

in which

R$^1$ is hydrogen, lower alkylamino, di(lower)alkylamino, cyano, halo, lower alkyl or halo; and
R$^2$ is hydrogen or cyano;

or a pharmaceutically acceptable salt thereof.

2. The process of claim 1 in which said compound or salt is orally administered.

3. A compound of the formula:

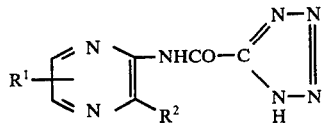

in which

R$^1$ is hydrogen, lower alkylamino, di(lower)alkylamino, cyano, halo, lower alkyl or halo; and
R$^2$ is hydrogen or cyano;

or a pharmaceutically acceptable salt thereof.

4. The compound of claim 3 which is N-(2-pyrazinyl)-1H-tetrazole-5-carboxamide or a pharmaceutically acceptable salt thereof.

5. The compound of claim 3 which is N-(5-dimethylaminopyrazin-2-yl)-1H-tetrazole-5-carboxamide or a pharmaceutically acceptable salt thereof.

6. The compound of claim 3 which is N-(3-cyanopyrazin-2-yl)-1H-tetrazole-5-carboxamide or a pharmaceutically acceptable salt thereof.

* * * * *